United States Patent [19]

Scheffel et al.

[11] Patent Number: 5,166,385
[45] Date of Patent: Nov. 24, 1992

[54] PROCESS FOR THE PREPARATION OF PHOSPHINO COMPOUNDS

[75] Inventors: Günter Scheffel, Burghausen; Stephen Lachhein, Hofheim am Taunus, both of Fed. Rep. of Germany

[73] Assignee: Hoechst Aktiengesellschaft, Frankfurt am Main, Fed. Rep. of Germany

[21] Appl. No.: 799,008

[22] Filed: Nov. 25, 1991

Related U.S. Application Data

[63] Continuation of Ser. No. 496,871, Mar. 21, 1990, abandoned.

[30] Foreign Application Priority Data

Mar. 23, 1989 [DE] Fed. Rep. of Germany ....... 3909564

[51] Int. Cl.$^5$ .............................................. C07F 9/02
[52] U.S. Cl. .................................... 558/89; 558/385; 560/76; 560/83; 564/15
[58] Field of Search .................... 558/89, 385; 560/76, 560/83; 564/15

[56] References Cited

U.S. PATENT DOCUMENTS 2,957,931 10/1960 Hamilton et al. .................. 558/137
4,399,287 8/1983 Baillie et al. ........................ 548/119

FOREIGN PATENT DOCUMENTS 0030424 6/1981 European Pat. Off.
1144275 6/1977 Fed. Rep. of Germany.

OTHER PUBLICATIONS

Hudson, R. F. "Structure and Mechanism in Organo-Phosphorus Chemistry" Academic Press, pp. 192–195 (1965).
Lowry et al. "Mechanism and Theory in Organic Chemistry" Harper & Row Pub. p. 89, 1976.
Houben-Weyl, Methoden der Organischen Chemie, Bd. Dec. 1, (1963), pp. 259–260, p. 14.
Chem. Berichte, Bd. 93, (1960), p. 1231.
Die Angewandte Makromolekulare Chemie 105, "Phosphorhaltige Polyethylenterephthalate", Volker Freudenberger and Franz Jakob, (1982), pp. 203–215.

Primary Examiner—C. Warren Ivy
Assistant Examiner—Celia Chang
Attorney, Agent, or Firm—Curtis, Morris & Safford

[57] ABSTRACT

Process for the preparation of phosphino compounds Phosphorus-containing compounds of the formula (I)

$$(R^1)(R^2)P(O)-CR^3R^4-CHR^5R^6 \qquad (I)$$

in which
$R^1$ and $R^2$ are alkyl, alkoxy or optionally substituted phenyl,
$R^3$ and $R^5$ are H, R, optionally substituted phenyl, ROCO—, RO—CO—RO—, halogen, CN, RO—, RO—RO—R-CO—, H$_2$NCO—, RNHCO— or RRNCO—, in which R is alkyl,
$R^4$ and $R^6$ have the same meaning as defined for $R^1$ and $R^2$ or are a divalent radical $$-CO-R^7-CO-$$

in which
$R^7$ is oxygen, NR* or sulfur, and R* is H, optionally substituted phenyl or alkyl, are precursors for plant protection agents and fire retardants. According to the invention they can be prepared in high yields and high purity by reacting a compound $(R^1)(R^2)P$—$OR^8$, in which $R^8$ is alkyl or optionally substituted phenyl, with an alkene of the formula $R^3R^4C$=$CR^5R^6$ and at least an equimolar amount of aprotic organic substance such as alcohols, amines, phenols, thiophenols or anilines.

15 Claims, No Drawings

PROCESS FOR THE PREPARATION OF PHOSPHINO COMPOUNDS

This application is a continuation of application Ser. No. 07/496,871, filed Mar. 21, 1990, now abandoned.

The invention relates to a process for the preparation of phosphino compounds of the formula (I)

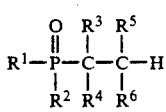

in which $R^1$ and $R^2$ independently of one another are alkyl, alkoxy or optionally substituted phenyl, $R^3$ and $R^5$ independently of one another are hydrogen, alkyl, unsubstituted phenyl or phenyl mono- or multisubstituted by halogen or mono- or disubstituted by alkoxy; or are alkoxycarbonyl, alkoxycarbonylalkoxy, halogen, cyano, alkoxy, alkoxyalkoxy, alkylcarbonyl, alkoxycarbonylalkyl, carbamoyl, alkylaminocarbonyl or dialkylaminocarbonyl, $R^4$ and $R^6$ independently of one another are hydrogen, alkyl, unsubstituted phenyl or phenyl mono- or multisubstituted by halogen or mono- or disubstituted by alkoxy; or are halogen, alkoxycarbonyl, alkoxycarbonylalkoxy, cyano, alkoxy, alkoxyalkoxy, alkylcarbonyl, alkoxycarbonylalkyl, carbamoyl, alkylaminocarbonyl or dialkylaminocarbonyl; or jointly are a divalent radical of the formula $$-CO-R^7-CO-,$$

in which

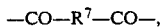

$R^7$ is oxygen, a radical of the formula NR*, in which R* represents hydrogen, $C_1-C_6$-alkyl, unsubstituted phenyl or phenyl mono- or multisubstituted by halogen; or is sulfur, which comprises reacting a compound of the formula (II)

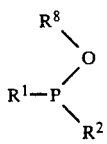

in which
$R^1$ and $R^2$ have the meanings defined above and
$R^8$ is alkyl or optionally substituted phenyl, together with a compound of the formula (III)

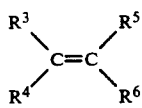

in which $R^3$, $R^4$, $R^5$, $R^6$ and $R^7$ have the meanings defined above,
and
with at least an equimolar amount of a protic organic substance except carboxylic acids.

The term 'alkyl' denotes, for example, a straight-chain, branched or cyclic alkyl such as methyl, ethyl, n- and i-propyl, n-, i-, t- and 2-butyl, pentyl isomers, hexyl isomers, cyclopentyl, cyclohexyl, heptyl and octyl isomers. The term 'alkoxy' denotes an alkyloxy radical comprising in the alkyl part the meanings cited above as examples of alkyl. The term 'optionally substituted phenyl' denotes an unsubstituted phenyl or a phenyl substituted, for example, by halogen, lower alkoxy or lower alkyl. The term 'halogen' denotes fluorine, chlorine, bromine and/or iodine, preferably chlorine.

Of particular interest is a process according to the invention, in which $R^1$ and $R^2$ independently of one another are $C_1-C_8$-alkyl, phenyl or $C_1-C_6$-alkoxy, preferably methyl, ethyl, phenyl, methoxy, ethoxy, propoxy or butoxy, in particular methyl, ethyl, phenyl, methoxy or ethoxy, $R^3$ and $R^5$ independently of one another are hydrogen, $C_1-C_6$-alkyl, unsubstituted phenyl or phenyl mono- or multisubstituted by halogen; or are $C_2-C_6$-alkoxycarbonyl, $C_2-C_6$-alkylcarbonyl, ($C_1-C_4$-alkyl)carbonyl-$C_1-C_{10}$-alkyl, halogen, cyano, $C_1-C_6$-alkoxy, ($C_1-C_4$-alkoxy)-$C_1-C_4$-alkoxy, carbamoyl, N-($C_1-C_4$-alkyl)aminocarbonyl, N,N-di($C_1-C_4$-alkyl)aminocarbonyl, 1-($C_1-C_4$-alkoxy)-1-hydroxymethyl or 1,1-bis($C_1-C_4$-alkoxy)methyl, $R^4$ and $R^6$ independently of one another are hydrogen, $C_1-C_6$-alkyl, unsubstituted phenyl or phenyl mono- or multisubstituted by halogen; or are $C_2-C_6$-alkoxycarbonyl, $C_2-C_6$-alkylcarbonyl, ($C_1-C_4$-alkyl)carbonyl-$C_1-C_{10}$-alkyl, halogen, cyano, $C_1-C_6$-alkoxy, ($C_1-C_4$-alkoxy)-$C_1-C_4$-alkoxy, carbamoyl, N-($C_1-C_4$-alkyl)aminocarbonyl, N,N-di($C_1-C_4$-alkyl)aminocarbonyl, 1-($C_1-C_4$-alkoxy)-1-hydroxymethyl or 1,1-bis($C_1-C_4$-alkoxy)methyl; or jointly are a divalent radical of the formula $$-CO-R^7-CO-,$$

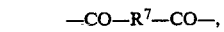

in which
$R^7$ is oxygen, a radical of the formula NR*, in which R* represents hydrogen, ($C_1-C_6$)-alkyl, unsubstituted phenyl or phenyl mono- to trisubstituted by halogen; or is sulfur.

The process according to the invention, in which
$R^1$ and $R^2$ independently of one another are methyl, ethyl, methoxy, ethoxy or phenyl,
$R^3$ is hydrogen,
$R^4$ is hydrogen or ($C_1-C_4$-alkoxy)carbonyl,
$R^5$ is hydrogen,
$R^6$ is hydrogen, halogen, cyano, ($C_1-C_4$-alkoxy)carbonyl or carbamoyl, preferably ($C_1-C_2$-alkoxy)carbonyl or cyano
is particularly preferred.

The compounds of the formula (I) are useful intermediates in the preparation of plant protection agents (see for example EP-A-30,424, U.S. Pat. No. 4,399,287) and fire retardants (Angewandte Makromolekulare Chemie 105, pp. 203–215 (1982) and literature cited therein). It is known that a few representatives of the compounds of the formula (I) are obtainable, for example, by reacting the compounds of the formula (II) with unsaturated fatty acids (see Houben-Weyl, Methoden der org. Chemie, volume 12/1, pp. 259–260 (1963) and literature cited therein). However, this process gives yields of only 10–50% which, because of the high amounts of effluent gases and waste products formed, represents a serious drawback both technically and ecologically. The unreacted phosphorus component (I) must undergo a costly process of disposal, since these compounds represent a fire and toxic hazard and have an objectionable smell (see Houben-Weyl, Methoden der org. Chemie, Vol. 12/1, p. 14). In addition, because of the poor yields, costly purification operations are needed at the end of the reaction.

In comparison with the known processes, the present invention relates to a highly selective, inexpensive and simple process which furnishes the phosphino compounds of the formula (I) in almost quantitative yields and in high purity.

The crude products obtained in an almost quantitative yield are usually so pure that they can be directly used for further chemical reactions.

For a number of reasons the process according to the invention is to be regarded as surprising. Thus, for example, the reactions of the phosphorus components (II) with the alkenes (III) do not give rise, according to examples in the literature, to the products (I) without resorting to a protic organic substance. Only highly viscous polymeric products are obtained (see Anionische Polymerisation, B. Vollmert, Grundriss der Makromolekularen Chemie, Springer-Verlag 1962, p. 107 ff and 159, see Comparison Example I). The low yields of up to a maximum of 50% in the examples described in the literature are likewise due to competing polymerization reactions as secondary reactions. The desired reactions are in some cases so slow that the polymerization becomes the main reaction. (Houben-Weyl, Methoden der org. Chemie, vol. 12/1, pp. 259-260). Surprisingly, the addition according to the invention of protic organic substances succeeds in substantially suppressing the polymerization and in forming the 1:1 adducts of the formula (I) in almost quantitative yields.

The process according to the invention is furthermore to be regarded as surprising inasmuch as it is precisely by the addition of protic organic substances to the reactions described in the literature in which phosphorus compounds of the formula (II) are reacted with unsaturated fatty acids that yields of less than 30% and hence even worse yields of the desired 1:1 adducts are obtained (see Comparison Example II).

The preferred protic organic substances are alcohols, in particular $C_1$–$C_6$-alcohols, for example, methanol, ethanol, propanol, isopropanol, n-, i-, t- and 2-butanol, further polyhydric alcohols such as ethanediol and glycerol, $C_1$–$C_6$-mercaptans, for example methylmercaptan, ethylmercaptan, propylmercaptan and 1,2-ethanedithiol, amines, in particular mono- or di($C_1$–$C_6$-alkyl)amines, for example methylamine, ethylamine, dimethylamine and propylamine, phenols, thiophenols, anilines and similar compounds and mixtures of these substances. Because the above substances can be generally regarded as "derivatives" of water on account of their protic properties, the process according to the invention cannot be carried out in the presence of water, in contrast to the organic protic compounds described, since water rapidly hydrolyzes the phosphorus components of the formula (II) (Sander, Chem. Ber. 93 (1960) 1223). Since it is quite impossible to obtain products of the formula (I) with water as the protic substance because of hydrolytic reactions taking place (see also Comparison Example III), it was unexpected for the protic organic substances to be used according to the invention to be suitable for achieving high selectivity and yields.

The protic organic substances R-H employed in the process according to the invention in at least equimolar amounts serve as reactants and, if appropriate, as solvents, and are converted, depending on the course of the reaction, at least in part, for example, to ethers, thioethers, amines, phenetoles, thiophenetoles or substituted anilines of the formula R—$R^8$, $R^8$ having the meaning defined above. The products R—$R^8$ are preferably removed from the reaction mixture during or at the end of the reaction, for example by distillation. Excess reactant or solvent R-H is preferably removed at the end of the reaction by vacuum distillation.

Carboxylic acids are likewise excluded from the process according to the invention. When in the process according to the invention organic acids, for example formic acid or acetic acid, are used as protic substances, virtually no products of the formula (I) are obtained (see Comparison Example IV). It follows that the protic organic substance must not possess too acidic characteristics. Whether a substance is suitable in the sense of the invention can be readily established in a preliminary experiment.

The procedure of the process according to the invention is for example such that the compounds of the formula (II) are dissolved in the protic organic substance and the alkenes (III) are added to the reaction mixture at temperatures between $-20°$ C. and $150°$ C., preferably between $0°$ and $100°$ C. It is also possible to add the components (II) and (III) to the protic organic substance at the same time.

It is equally possible to start with a mixture of the alkene component (III) and the protic organic substance and add the phosphorus component (II) to this solution.

The protic organic substances are used in at least equimolar amounts. In amounts greater than equimolar they can be additionally employed in the sense of an organic solvent.

The process may be carried out without solvent or with excess protic organic substance as solvent and/or in the presence of customary organic solvents which are inert under the reaction conditions. Examples of the last-named solvents are solvents such as optionally halogenated, aliphatic, cycloaliphatic, aromatic or araliphatic hydrocarbons, aliphatic or cycloaliphatic ethers, for example polyglycol dialkyl ethers, as well as ketones and esters. It is expedient to perform the process in an inert gas atmosphere, for example under nitrogen, in order to prevent oxygen interfering with the reaction.

The process according to the invention may be continuous or discontinuous.

The process according to the invention is elucidated in greater detail by the examples below.

EXAMPLE 1

Methyl 3-(methoxy-methylphosphinyl)propionate 80 g of methanol are mixed at room temperature under nitrogen with 216 g of dimethyl methanephosphonate and the mixture is treated dropwise at room temperature with 172 g of methyl acrylate, the temperature rising to $70°$ C. At the end of the dropwise addition the mixture is further stirred for 1 hour, at the end of which period about 90 g of dimethyl ether have separated in a fitted cooling trap. Excess methanol used as solvent is then removed by vacuum distillation. The crude product is obtained in a yield of 365 g with a 96.4% purity, which represents a theoretical yield of 97.7%. The boiling point of a distilled sample is $96°$ C. at 0.027 mbar. The $^1$H-NMR spectrum and the CHP analysis of the product correspond to those of a comparison sample, synthesized by an independent route.

EXAMPLE 2

Ethyl 3-(methoxy-methylphosphinyl)propionate

A flask filled with nitrogen and fitted with a cooling trap is charged with 216 g of dimethyl methanephosphonate; the contents are heated to 60° C. and a mixture of 200 g of ethyl acrylate and 100 g of methanol is added dropwise in the course of 1 hour, the temperature rising to 65° C. The reaction mixture is further stirred for 1 hour, during which period a total of 91 g of dimethyl ether are collected in the cooling trap. Excess methanol is removed by vacuum distillation. The crude product is obtained in a yield of 362 g with a 97.3% purity, which corresponds to a theoretical yield of 97.9%. The boiling point of a sample is 100°–102° C. at 0.013 mbar.

EXAMPLE 3

Methyl 3-(methoxy-methylphosphinyl)propionate

A mixture of 86 g of methyl acrylate and 80 g of ethanol is added dropwise in the course of 30 minutes at 60° C. under nitrogen to a solution of 108 g of dimethyl methanephosphonate. The reaction mixture is then stirred at 60° C. for one hour. A total of 55 g of methyl ethyl ether are collected in the cooling trap. Excess ethanol is then removed by vacuum distillation. The crude product is obtained in a yield of 184 g with a 95.4% purity, which corresponds to a theoretical yield of 97.5%.

EXAMPLE 4

3-(Methoxy-ethylphospinyl)propionamide 71 g of acrylamide and 120 g of n-propylamine are mixed at room temperature under nitrogen and the mixture is heated to 50° C. 122 g of dimethyl ethanephosphonate are added dropwise to the reaction solution in the course of 30 minutes. The reaction mixture is then stirred for 5 hours at reflux temperature and the solvent (low-boiling solvent such as excess propylamine + N-methyl-N-propylamine) is removed by vacuum distillation. The crude product is obtained in a yield of 175 g with a 94.4% purity, which corresponds to a theoretical yield of 92.3%.

The $^1$H-NMR spectrum and the CHP analysis of the product are in agreement with the corresponding data of a comparison sample, synthesized by an independent route.

EXAMPLE 5

3-(Ethoxy-proplyphosphinyl)propionitrile 53 g of acrylonitrile are added dropwise under nitrogen at a reaction temperature of 70° C. to a mixture of 160 g of diethyl propanephosphonate in 100 g of n-propylmercaptan in the course of 2 hours. After a further 3 hours the solvent (low-boiling solvent such as $C_3H_7SC_2H_5$ and excess $C_3H_7SH$) is removed by vacuum distillation; the crude product is obtained in a yield of 173 g with a 95.4% purity, which corresponds to a theoretical yield of 94.4%. The boiling point of the product is 117°–118° C. at 0.027 mbar.

EXAMPLE 6

Ethyl 3-(ethoxycarbonyl)-3-(ethoxy-ethylphosphinyl)propionate 172 g of diethyl fumarate are slowly added at 65°–70° C. under nitrogen to a mixture of 140 g of diethyl ethanephosphonate in 46 g of ethanol. After a further 3 hours the solvent (excess ethanol and diethyl ether) is removed by vacuum distillation; the crude product is obtained in a yield of 285 g with a 95.7% purity, which corresponds to a theoretical yield of 90.9%.

The $^1$H-NMR spectrum and the CHP analysis are in agreement with the corresponding data of a comparison sample, synthesized by an independent route.

EXAMPLE 7

Methyl 3-(dimethoxyphosphinyl)propionate 86 g of methylacrylate and 100 g of isobutanol are mixed under nitrogen at room temperature and heated to 80° C. 124 g of trimethylphosphite are added dropwise to the reaction solution in the course of 1 hour. The reaction mixture is stirred for 5 hours at reflux temperature and the solvent (remainder of isobutanol and isobutyl methyl ether) is removed by vacuum distillation. The crude product is obtained in a yield of 173 g with a 94.1% purity, which corresponds to a theoretical yield of 83.0%. The boiling point is 104°–106° C. at 0.93 mbar.

EXAMPLE 8

3-(Dimethylphosphinyl)propionitrile 135 g of isobutyl dimethylphosphinate are slowly added under nitrogen at 20° C. to a mixture of 53 g of acrylonitrile and 32 g of methanol, the temperature rising slowly to about 60° C. The reaction mixture is heated for about 3 hours and the solvent (remainder of methanol and isobutyl methyl ether) is removed by distillation. The crude product is obtained in a yield of 125 g with a 95.3% purity, which corresponds to a theoretical yield of 90.9%. The boiling point of a distilled sample is 98°–100° C. at 0.013 mbar.

EXAMPLE 9

Methyl 3-(dimethylphosphinyl)-3-methoxycarbonyl)propionate 135 g of isobutyl dimethylphosphinate and 144 g of dimethyl maleate are added under nitrogen simultaneously dropwise from two separate dropping funnels at about 70° C. to a solution of 67 g of ethylene glycol. After a further hour the reaction mixture is distilled under reduced pressure, i.e. volatile constituents are carefully removed by vacuum distillation. The crude product is obtained in a yield of 215 g with a 95.2% purity, which corresponds to a theoretical yield of 91.8%.

The $^1$H-NMR spectrum and the CHP analysis correspond to a comparison sample synthesized by an independent route. The boiling point of the product is 128°–130° C. at 0.013 mbar.

EXAMPLE 10

Methyl 3-(phenyl-methoxyphosphinyl)-2-chloropropionate 138 g of dimethyl phenylphosphonate are slowly added at 20° C. under nitrogen to a solution of 120.5 g of methyl 2-chloroacrylate and 94 g of phenol. After a reaction time of 3 hours at 70° C. phenetole is removed by vacuum distillation. The residue represents 267 g of crude product with a 93.0% purity, which corresponds to a theoretical yield of 90.1%.

The $^1$H-NMR spectrum and the CHP analysis of the product correspond to those of a comparison sample, synthesized by an independent route.

COMPARISON EXAMPLE I without protic organic substance 86 g of methyl acrylate are added to 108 g of dimethyl methanephosphonate at 70° C. and the reaction mixture is heated at 70° C. for a further 4 hours. The reaction mixture is worked up by vacuum distillation, yielding 194 g of a highly viscous oil which according to the $^1$H-NMR and $^{31}$P-NMR spectra does not contain the desired methyl 3-(dimethylphosphinyl)propionate. If the reaction mixture is worked up by distillation, no distillable product is obtained, which points to polymerization occurring in the experiment.

COMPARISON EXAMPLE II in accordance with examples from the literature (Houben-Weyl, Methoden der org. Chemie, volume 12/1, pp. 259-260 and literature cited therein)

108 g of dimethyl methanephosphonate are added dropwise at 70° C. to a solution of 86 g of methacrylic acid and 32 g of methanol in the course of 30 minutes. After a reaction time of 3 hours the reaction mixture is worked up by vacuum distillation. 59 g of 3-(dimethylphosphinyl)-2-methylpropionic acid are obtained with a 91.1% purity, which corresponds to a theoretical yield of 29.5%.

COMPARISON EXAMPLE III in the presence of water as protic substance 108 g of dimethyl methanephosphonate are added dropwise at an initial temperature of 25° C. to a solution of 86 g of methylacrylate and 20 g of water in the course of 30 minutes. The temperature rises to 65° C. during the addition. The reaction mixture is then heated for 3 hours at 70° C.

After working up of the reaction mixture by vacuum distillation, no methyl 3-(dimethylphosphinyl)propionate is obtained. On the other hand the hydrolysis product methyl methanephosphonate, which could be isolated in an amount of 91 g by distillation, is obtained in a yield of 91.4% with a 94.4% purity. The boiling point of the distilled sample is 55°-58° C. at 10-15 torr. The $^1$H-NMR spectrum and the CHP analysis correspond to the compound obtained from a comparison sample, synthesized by an independent route.

COMPARISON EXAMPLE IV in the presence of formic acid as protic polar substance 108 g of dimethyl methanephosphonate are added dropwise at 70° C. to a solution of 86 g of methylacrylate and 50 g of formic acid in the course of 2 hours and the reaction mixture is heated at 70° C. for 2 hours. After working up the reaction mixture by vacuum distillation, 123 g of a crude product are obtained which from its $^1$H-NMR and $^{31}$P-NMR spectra and gas chromatographic analysis contains none of the desired product. The reaction mixture is composed of several substances, the bulk of them being acid compounds of phosphorus in the oxidation stage V.

We claim:

1. A process for the preparation of compounds of the formula (I), $$R^1R^2PO\text{—}CR^3R^4\text{—}CR^5R^6\text{—}H \qquad (I)$$

in which
  $R^1$, $R^2$ independent of one another are $C_1$-$C_6$-alkyl, $C_1$-$C_6$-alkoxy, phenyl or phenyl substituted by halogen, lower alkoxy or lower alkyl,
  $R^3$ is hydrogen or ($C_1$-$C_4$-alkoxy)-carbonyl,
  $R^4$ is hydrogen or ($C_1$-$C_4$-alkoxy)-carbonyl,
  $R^5$ is hydrogen or chloro and,
  $R^6$ is cyano, ($C_1$-$C_4$-alkoxy)-carbonyl or carbamoyl,
which comprises reacting a compound of the formula (II), $$R^1R^2P\text{—}O\text{—}R^8 \qquad (II)$$

in which
  $R^1$, $R^2$ have the meaning defined above and
  $R^8$ is alkyl, together with a compound of the formula (III), $$R^3R^4C{=}CR^5R^6 \qquad (III)$$

in which
  $R^3$, $R^4$, $R^5$ and $R^6$ have the meanings defined above, and with at least an equimolar of a protic organic substance selected from the group consisting of alcohols, polyhydric alcohols, mercaptans, amines, phenols, thiophenols, anilines and mixtures of these compounds.

2. A process as claimed in claim 1 wherein
  $R^1$ is methoxy, ethoxy or methyl,
  $R^2$ is methoxy, methyl, ethyl, propyl or phenyl,
  $R^3$ is hydrogen or ($C_1$-$C_4$-alkoxy)-carbonyl,
  $R^4$ is hydrogen or ($C_1$-$C_4$-alkoxy)-carbonyl,
  $R^5$ is hydrogen or chloro and,
  $R^6$ is cyano, ($C_1$-$C_4$-alkoxy)-carbonyl or carbamoyl, and
  $R^8$ is $C_1$-$C_4$-alkyl.

3. A process as claimed in claim 1, wherein the protic organic substance is methanol, ethanol, propanol, isopropanol, n-, i-, t- or 2-butanol, ethandiol, methylamine, ethylamine, propylamine, dimethylamine, methylmercaptan, ethylmercaptan, propylmercaptan or phenol.

4. The process as claimed in claim 1,
  wherein the temperature for the reaction of the compounds (II) and (III) is between −20° C. and 150° C.

5. The process as claimed in claim 4, wherein the temperature for the reaction of the components (II) and (III) is between 0° C. and 100° C.

6. The process as claimed in claim 1, wherein the process is carried out in the customary organic solvents or mixtures thereof.

7. The process as claimed in claim 6, wherein excess protic organic substance is used as organic solvent.

8. The process as claimed in claim 1, wherein the reaction is performed in an inert gas atmosphere.

9. The process as claimed in claim 2, wherein alcohols, mercaptans, amines, phenols, thiophenols or anilines or mixtures of these substances are used as protic organic substances.

10. The process as claimed in claim 4, wherein alcohols, mercaptans, amines, phenols, thiophenols or anilines or mixtures of these substances are used as protic organic substances.

11. The process as claimed in claim 2, wherein the temperature for the reaction of the compounds (II) and (III) is between −20° C. and 150° C.

12. The process as claimed in claim 2, wherein the temperature is between 0° and 100° C.

13. The process as claimed in claim 11, wherein excess protic organic substance is used as organic solvent.

14. The process as claimed in claim 12, wherein excess protic organic substance is used as organic solvent.

15. A process as claimed in claim 1, wherein in the protic organic substance is selected from the group consisting of $C_1$–$C_6$-alcohols, ethanediol, glycerol, $C_1$–$C_6$-mercaptans mono- or di-($C_1$–$C_6$-alkyl)-amines, phenols, thiophenols and anilines and mixtures of these compounds.

* * * * *